(12) United States Patent
Prajapati et al.

(10) Patent No.: US 10,166,197 B2
(45) Date of Patent: Jan. 1, 2019

(54) SUGAR ESTER NANOPARTICLE STABILIZERS

(71) Applicant: St. John's University, Queens, NY (US)

(72) Inventors: Hetalben N. Prajapati, New Milford, NJ (US); Abu T. M. Serajuddin, Flushing, NY (US)

(73) Assignee: St. John's University, Queens, NY (US)

( * ) Notice: Subject to any disclaimer, the term of this patent is extended or adjusted under 35 U.S.C. 154(b) by 0 days.

(21) Appl. No.: 15/042,282

(22) Filed: Feb. 12, 2016

(65) Prior Publication Data

US 2016/0235687 A1 Aug. 18, 2016

Related U.S. Application Data

(60) Provisional application No. 62/116,071, filed on Feb. 13, 2015.

(51) Int. Cl.

| | | |
|---|---|---|
| *A61K 31/10* | (2006.01) |
| *A61K 31/58* | (2006.01) |
| *A61K 31/216* | (2006.01) |
| *A61K 31/196* | (2006.01) |
| *A61K 31/496* | (2006.01) |
| *A61K 31/7024* | (2006.01) |
| *A61K 9/51* | (2006.01) |
| *A61K 9/107* | (2006.01) |
| *A61K 9/14* | (2006.01) |
| *A61K 9/16* | (2006.01) |

(52) U.S. Cl.
CPC .......... *A61K 9/5123* (2013.01); *A61K 9/1075* (2013.01); *A61K 9/145* (2013.01); *A61K 9/1623* (2013.01); *A61K 9/5192* (2013.01); *A61K 31/10* (2013.01); *A61K 31/196* (2013.01); *A61K 31/216* (2013.01); *A61K 31/496* (2013.01); *A61K 31/58* (2013.01)

(58) Field of Classification Search
CPC .... A61K 31/10; A61K 31/196; A61K 31/216; A61K 31/496; A61K 31/58; A61K 6/1075; A61K 9/145; A61K 9/1623; A61K 9/5192

See application file for complete search history.

(56) References Cited

U.S. PATENT DOCUMENTS

| | | |
|---|---|---|
| 5,145,684 A | 9/1992 | Liversidge et al. |
| 5,302,401 A | 4/1994 | Liversidge et al. |
| 5,336,507 A | 8/1994 | Na et al. |
| 5,340,564 A | 8/1994 | Illig et al. |
| 5,399,363 A | 3/1995 | Liversidge et al. |
| 5,429,824 A | 7/1995 | June |
| 5,494,683 A | 2/1996 | Liversidge et al. |
| 5,510,118 A | 4/1996 | Bosch et al. |
| 5,518,187 A | 5/1996 | Bruno et al. |
| 5,518,738 A | 5/1996 | Eickhoff et al. |
| 5,552,160 A | 9/1996 | Liversidge et al. |
| 5,560,931 A | 10/1996 | Eickhoff et al. |
| 5,565,188 A | 10/1996 | Wong et al. |
| 5,569,448 A | 10/1996 | Wong et al. |
| 5,571,536 A | 11/1996 | Eickhoff et al. |
| 5,591,456 A | 1/1997 | Franson et al. |
| 5,593,657 A | 1/1997 | Ruddy et al. |
| 5,622,938 A | 4/1997 | Wong |
| 5,718,388 A | 2/1998 | Czekai et al. |
| 5,718,919 A | 2/1998 | Ruddy et al. |
| 5,862,999 A | 1/1999 | Czekai et al. |
| 6,045,829 A | 4/2000 | Liversidge et al. |
| 6,068,858 A | 5/2000 | Liversidge et al. |
| 6,153,225 A | 11/2000 | Lee et al. |
| 6,375,986 B1 | 4/2002 | Ryde et al. |
| 2008/0138424 A1 | 6/2008 | Ryde et al. |
| 2011/0064812 A1 | 3/2011 | Bahl et al. |
| 2012/0244134 A1 | 9/2012 | Chen et al. |

FOREIGN PATENT DOCUMENTS

| | | |
|---|---|---|
| WO | 2007/062266 A2 | 5/2007 |
| WO | 2012/108631 A2 | 8/2012 |

OTHER PUBLICATIONS

Horspool et al., "Advancing new drug delivery concepts to gain the lead," Drug Delivery, 3(7):34-46 (2003).

Kim et al., "Effective polymeric dispersants for vacuum, convection and freeze drying of drug nanosuspensions," Int'l J. of Pharmaceutics, 397:218-224 (2010).

Li et al., "Formulation, biological and pharmacokinetic studies of sucrose ester-stabilized nanosuspensions of oleanolic acid," Pharm. Res. 28(8):2020-33 (2011).

Liu et al., "Nanosuspensions of poorly soluble drugs: Preparation and development by wet milling," Int. J. of Pharmaceutics 411:215-222 (2011).

Chan et al., "Production methods for nanodrug particles using the bottom-up approach," Adv. Drug Del. Rev. 63 (6):406-416 (2011).

*Primary Examiner* — Shengjun Wang

*Assistant Examiner* — Jody L Karol

(74) *Attorney, Agent, or Firm* — Venable LLP

(57) ABSTRACT

Solid dosage forms containing nanoparticles are prepared where sugar esters serve as nanoparticle stabilizers that prevent agglomeration of nanoparticles during preparation of the solid dosage form and allow for restoration of the original nanoparticle size of the nanoparticles upon redispersion of the solid dosage form in aqueous media.

15 Claims, 12 Drawing Sheets

Figure 7A
Figure 7B
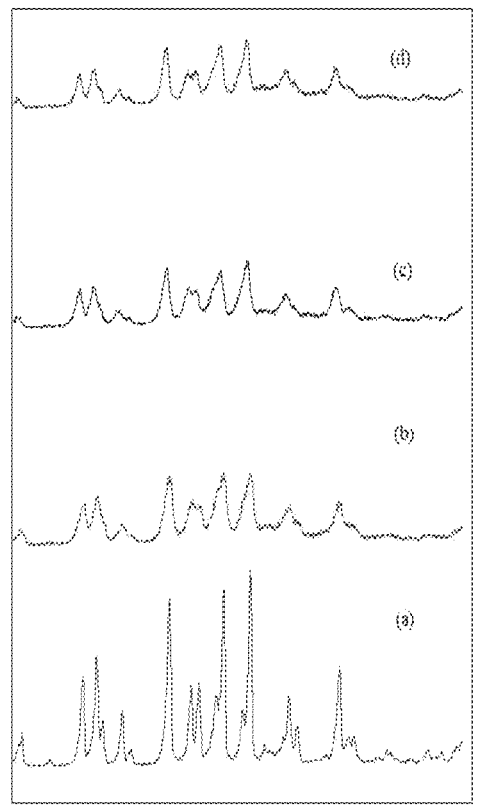
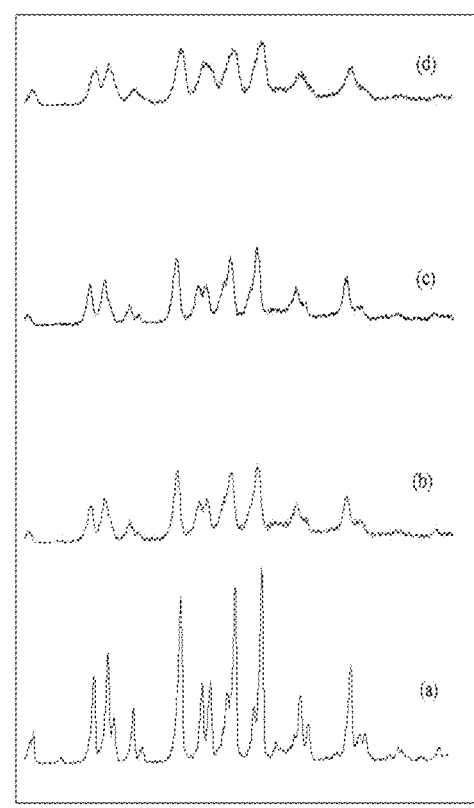

Figure 8A
Figure 8B
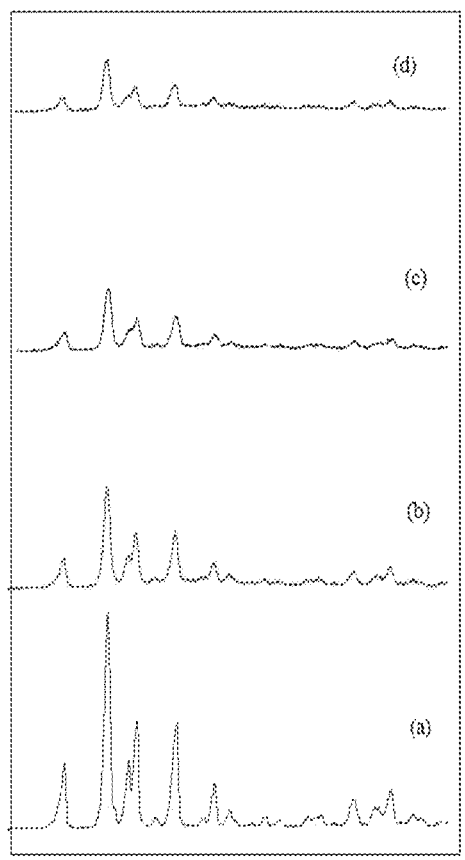
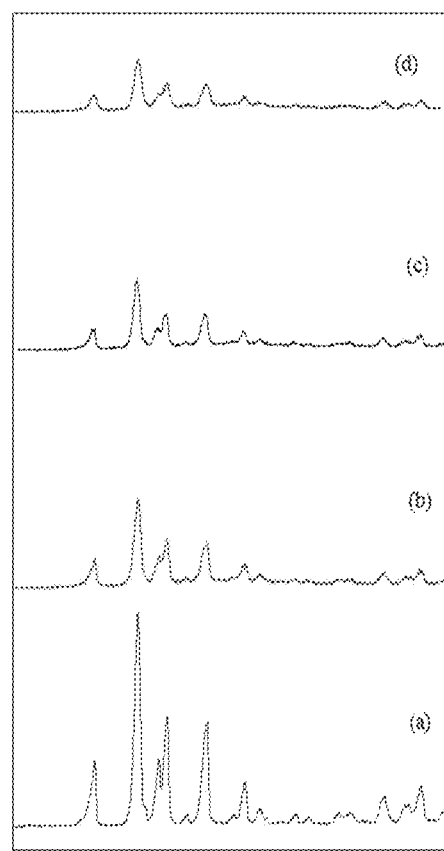

Figure 11A
Figure 11B
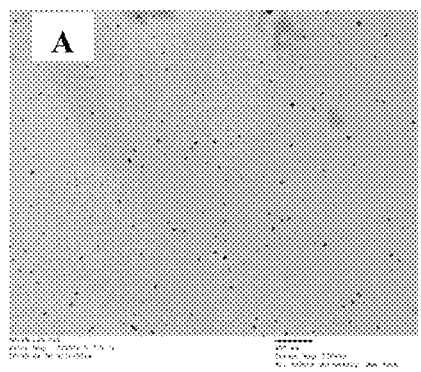
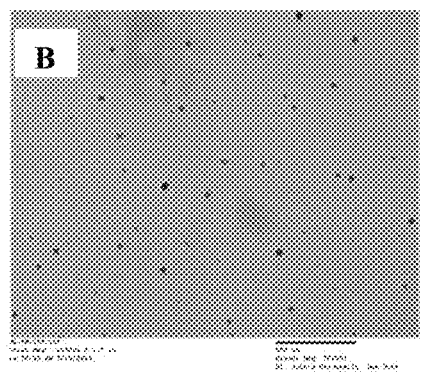
Figure 11C
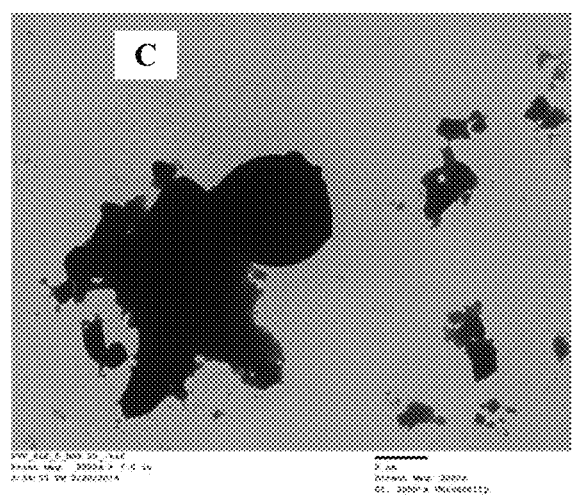

SUGAR ESTER NANOPARTICLE STABILIZERS

TECHNICAL FIELD

This invention relates to a process of preparing nanoparticulate pharmaceutical formulations using sugar ester nanoparticle stabilizers. This invention also relates to a solid dosage form containing nanoparticles prepared by said process.

BACKGROUND

Over the past two decades, the majority of drug candidates discovered by the pharmaceutical industry have been extremely insoluble in water. Indeed, two out of three compounds selected for development as drug products are very poorly water-soluble. Horspool et al., "Advancing new drug delivery concepts to gain the lead," Drug Delivery, Vol. 3, pp. 34-46 (2003). Poor water solubility leads to low solubility in gastrointestinal fluids, thereby limiting the dissolution rate of the drug products in the gastrointestinal tract. Accordingly, formulation of such compounds often leads to drug products with incomplete and variable bioavailability and suboptimal clinical efficacy. The bioavailability of these compounds could also be susceptible to food effect.

In recent years, the conversion of drug particles from the micrometer range (microparticles) to the nanometer range (nanoparticles) has emerged as a very attractive approach for enhancing the dissolution rate and the bioavailability of poorly water-soluble drugs. Through particle size reduction to the nanometer range, the surface areas of the drug particles are dramatically increased, thereby resulting in higher dissolution rates and, consequently, higher oral bioavailability. Nanoparticle formulations are usually prepared as liquid nanosuspensions by dispersing nanocrystals in an aqueous media. Liquid nanosuspensions can also be referred to sub-micron colloidal dispersions of drug particles stabilized by surfactants, polymers, or combinations of both.

While nanoparticles are usually produced as liquid nanosuspensions, solid oral dosage forms (e.g., tablets, softgel capsules, hard-shell capsules, and pellets) are the first choice for the development of drug products due to various advantages, such as ease of handling, ease of administration, physical stability and/or patient convenience. To obtain solid, dry drug particles for incorporation into solid oral dosage forms, liquid formulations should be transformed into powder by drying. Generally, the transformation of liquid nanosuspensions into dry solids can be achieved by, for example, tray drying, vacuum drying, lyophilization, spray drying, freeze drying, and spray granulation.

Despite the advantages of solid oral dosage forms, formulating oral solid dosage forms containing nanoparticles has been challenging for formulation scientists for many years. Indeed, among the nanocrystalline products available on the market, only four were developed as solid dosage forms (i.e., Rapamune®, Emend®, Tricor®, and Triglide®), which suggests that there are technical challenges associated with formulating solid oral dosage forms containing nanoparticles. A primary problem in formulating oral solid dosage forms containing nanoparticles is the propensity for the nanoparticles to agglomerate during preparation due to interparticulate interactions and during the drying process of converting the liquid nanosuspension to dry solids. For effective application of nanotechnology to increase dissolution rate and, therefore, bioavailability of poorly water-soluble drugs, it is important that there is no irreversible agglomeration of nanoparticles during drying. Since nanoparticles can spontaneously increase in particle size due to agglomeration, measures must be taken to stabilize them so as to ensure that the surfaces areas of the drug particles are not decreased resulting in lower dissolution rates. A further problem relates to "redispersibility" of the dry solids. It is important that the drug particles return to their original nanoparticle size when the dry solids are redispersed in aqueous fluids, such as digestive juices, after oral administration. If the drug particles are not able to redisperse into the particle size of the original nanosuspension, they will compromise the dissolution rate once in contact with gastrointestinal fluid. This "redispersibility" is essential in order to attain the expected pharmaceutical performances of the drug products. Similarly, the original nanoparticle size should be restored if the dry solids are resuspended in aqueous media for parenteral administration or other routes of administration.

Typically, these problems regarding agglomeration and redispersibility are addressed through inclusion of a significant amount of excipients in the dosage forms, such as stabilizers, cryoprotectants, lyoprotectants, bulking agents, and dispersing agents. See, e.g., Kim et al. "Effective polymeric dispersants for vacuum, convection, and freeze drying of drug nanosuspensions," Int'l J. of Pharmaceutics, 397, 218-224 (2010). These excipients stabilize nanoparticles by either electrostatic repulsion or steric stabilization via charged stabilizers or non-ionic surfactants/polymers. Examples of commonly used nanoparticle stabilizers in the art include sugar alcohols, water-soluble polymers, polymeric stabilizers, such as povidones, pluronics, and cellulosics (e.g., HPMC and HPC), and surfactants, such as polysorbate 80, lecithins, cholic acid derivatives, and sodium lauryl sulfate ("SLS"). However, in order to overcome the aforementioned problems, the amount of excipients is usually more than the actual drug content, thereby limiting drug loading and compromising the integrity of the final dosage form. In addition, with regard to redispersibility, sonication may be necessary to reduce the particle size of the dry solids redispersed in aqueous media.

Accordingly, there is currently a need in the state of the art for an oral solid dosage form containing nanoparticles that is produced without the need for a significant amount of excipients that would compromise drug loading. In addition, there is a need for an oral solid dosage form containing nanoparticles that exhibits redispersibility without the need for sonication, since sonication is not a physiological condition.

U.S. Pat. Nos. 5,145,684, 5,518,187, 5,862,999, 5,510,118, 5,336,507, 5,340,564, 5,399,363, 5,494,683, 5,429,824, 5,552,160, 5,560,931, 5,565,188, 5,569,448, 5,571,536, 5,591,456, 5,593,657, 5,622,938, 5,718,388, 5,718,919, 6,045,829, 6,068,858, and 6,153,225 describe methods of preparing nanosuspensions. However, in contrast to the present invention, these publications fail to address the issue of the conversion of the nanosuspensions to dry solids and the subsequent redispersion into nanoparticles.

U.S. Pat. No. 5,518,738 describes the dispersion of nanoparticulate naproxen and PVP (K29/32) in water. Redispersants such as hygroscopic sugar, sodium lauryl sulfate ("SLS"), hygroscopic sugar+SLS, dioctyl sodium sulfosuccinate ("DOSS") were added to the dispersion individually and dried in the oven to produce solid films. However, these formulations showed extremely poor redispersibility.

U.S. Pat. No. 6,375,986 refers to the problem of redispersibility of solid nanoparticulate formulations to their original particle size and discloses that the combination of at least one polymeric stabilizer (PVP) and surfactant exhibits redispersibiltiy of nanoparticulate compositions upon administration to a mammal. However, the mean particle size of redispersion was still higher than the mean particle size of the original nanosuspension even after one minute of sonication. Accordingly, this publication, in contrast to the present invention, fails to demonstrate redispersion into the particle size of the original nanosuspension.

U.S. Patent Application Publication No. 2008/0138424 describes nanoparticulate fenofibrate formulations containing 5% w/w of drug, 1% w/w of hypromellose, and 0.05% w/w of DOSS, resulting in nanosuspensions having particle size of 139 nm (90%<266 nm) with wet media milling. Redispersibility of spray granulated powders of preferred nanoparticulate fenofibrate compositions comprising hypromellose and DOSS with or without SLS was performed in DI water and particle size of resultant nanosuspensions was reported as 390 nm (D90=418 nm) and 182 nm (D90=260 nm), respectively. However, these spray granulated powders contain sucrose at 1:0.6 and 1:1 (drug:sucrose) ratios, respectively. When a nanoparticulate fenofibrate tablet formulation was formulated, a granulated feed dispersion (GFD) was first prepared by combining the nanoparticulate fenofibrate dispersion with sucrose, SLS, docusate sodium and purified water, The GFD was then sprayed onto lactose monohydrate to get a spray granulated intermediate (SGI), and finally the SGI was mixed with additional excipients like microcrystalline cellulose, crospovidone and magnesium before compression into tablets. This formulation was subjected to assess the effect of food on the bioavailability of a nanoparticulate fenofibrate. The formulation and the manufacturing process, unlike the present invention, were very complex and required large amounts of excipients. Also, redispersibility studies were not reported for tablet formulation. It was noted that "the compositions redisperse such that the effective average particle size of the redispersed fibrate particles is less than about 2 microns", which merely indicates that the compositions did not redisperse to their original particle sizes.

U.S. Pat. No. 5,302,401 has addressed the issue of agglomeration of nanoparticles during lyophilization and described a composition comprised of nanoparticles having a surface modifier adsorbed on the surface thereof and a cryoprotectant associated therewith to prevent agglomeration during lyophilization. The nanodispersions (containing danazol and 1.5% w/w PVP) having a mean particle size of 250 nm was unable to redisperse into particle size of the original nanosuspension and showed a significant increase in the number of particles above 10 μm in the reconstituted dispersion. The addition of sucrose to the danazol/PVP solution substantially reduced particle size growth during lyophilization compared to the nanosuspension which was lyophilized without sucrose. However, the redispersed system had particle size D10 value of 6368 μm compared to original nanosuspension with D10 value of 1122 μm. When mannitol was incorporated (2% mannitol) instead of sucrose, before lyophilization, the particle size redispersed system was observed as 19196 μm.

U.S. Pat. No. 6,045,829 describes formulations of nanoparticulate HIV protease inhibitors comprising a cellulosic surface stabilizer and a dry film nanoparticulate composition. However, the nanoparticulate formulation is mixed with sugar before drying with a drug to sugar ratio of, preferably, between 5:3 and 14:10.

U.S. Patent Application Publication No. 2011/0064812 A1 describes an oral solid dosage form containing nanoparticles in a solution containing fish gelatin to form a nanosuspension and freeze-drying the nanosuspension. However, sugar (especially mannitol) is incorporated as bulking agent in nanosuspension before freeze drying. In the '812 publication, in vitro and in vivo performances of solid dosage forms produced were attributed to their disintegration times. According to the inventors, "the disintegration time targeted for a product made using the present invention can be manipulated to achieve specific disintegration properties that suit pharmacokinetic needs as well as patient requirements." However, no data on in vitro-in vivo correlation was provided. There was also no determination of the particle size of material after disintegration of dosage forms, since sonication was used "for analysis of all nanosuspensions and solid dosage form testing."

WO 2007/062266 A2 describes ganaxolone formulations wherein the volume weighted median diameter (D50) of the particles is from about 50 nm to about 500 nm. The ganaxolone formulations are composed of HPMC, SLS, and sucrose and were dried by rotary evaporation and spray layered onto sucrose or microcrystalline cellulose beads. These dried samples showed agglomeration, as redispersion did not result in the original size and had D50 values in the range of 11-25 micrometers. Further, a minute of sonication did not return D50 to its original value.

U.S. Patent Application Publication No. 2012/0244134 A1 describes a process for preparing an aqueous dispersion using a complex stabilizer having an HLB value of about 10 to about 17. The complex stabilizer is comprised of lecithin and at least one non-phospholipid selected from polysorbate, sugar esters, and polyglycerol fatty acid ester. Only sucrose ester with a long chain fatty acid (sucrose stearate) is used. There is, however, no disclosure or suggestion of using sucrose fatty acid esters as a stabilizer for preventing agglomeration during drying or whether redispersion into original nanosuspension particle size occurred. All particle size analysis was conducted after ultrasonication for 5 minutes.

WO 2012/108631 A2 describes wet milling processes to generate nanoparticles of a water insoluble active ingredient with a certain polymer, an organic or inorganic acid, and, optionally, a surfactant. While sucrose fatty acid esters are included in a list of surfactants, there is no disclosure or suggestion of using sucrose fatty acid esters as nanoparticle stabilizers during the preparation of nanoparticles and also during the drying process.

Li et al. reported preparation of nanosuspensions of a drug, oleanolic acid, by using two sugar esters having long-chain fatty acids, sucrose laurate and sucrose palmitate, as surfactants. "Formulation, biological and pharmacokinetic studies of sucrose ester-stabilized nanosuspensions of oleanolic acid," Pharm. Res. 28(8):2020-33 (2011). The sugar esters were used either alone or as blends, and the relative ratios of the sugar ester to the drug was very high ranging from 10:1 w/w to 2:1 w/w. An emulsion/solvent evaporation method was used to prepare the nanosuspensions. However, the method was complex and not all the drug converted to nanoparticles. In the last two steps of the process, the suspensions were centrifuged to remove excess undissolved materials, and the supernatant was passed through a 0.22 μm membrane filter to give a visually clear nanosuspension. Since the primary focus of the study was biological and pharmacokinetic evaluation of nanoparticles, the filtered suspensions were used for further studies. Although freeze-drying of the filtered suspensions was mentioned, no redispersibility test of the dried materials was performed, and no data were provided.

By providing for a novel preparation of oral solid dosage forms containing nanoparticles wherein sugar ester derivatives serve as nanoparticle stabilizers, the present invention advances the state of the art.

SUMMARY OF THE INVENTION

The present invention is directed to a novel method for preparing a solid dosage form containing nanoparticles, the method comprising the steps of: (a) reducing the particle size of at least one pharmaceutically active ingredient dispersed in a solution containing a sugar ester nanoparticle stabilizer to form a nanosuspension; and (b) drying the nanosuspension of step (a) to form the solid dosage form.

The present invention is also directed to a novel solid dosage form containing nanoparticles made by a method comprising the steps of: (a) reducing the particle size of at least one pharmaceutically active ingredient dispersed in a solution containing a sugar ester nanoparticle stabilizer to form a nanosuspension; and (b) drying the nanosuspension of step (a) to form the solid dosage form.

The present invention is also directed to a novel nanosuspension comprising nanoparticles of at least one pharmaceutically active ingredient dispersed in a solution containing a sugar ester nanoparticle stabilizer.

In preferred embodiments, the sugar ester nanoparticle stabilizer is a sugar fatty acid ester, more preferably the sugar fatty acid ester comprises a medium chain fatty acid, still more preferably the medium chain fatty acid is selected from the group consisting of caproic acid, caprylic acid, capric acid, lauric acid, fatty acids with aliphatic tails of 6 to 12 carbons, and combinations thereof, and most preferably the sugar fatty acid ester is sucrose laurate or lactose laurate. In certain embodiments, the sugar ester nanoparticle stabilizer is a combination of more than one sugar fatty acid ester, and while excipients other than the sugar ester nanoparticle stabilizer may be added for purposes other than stabilizing the nanoparticles, no additional excipients for stabilizing the nanoparticles are present.

In a preferred embodiment, the particle size of the at least one pharmaceutically active ingredient after step (a) but prior to step (b) is an original nanoparticle size, and the particle size of the at least one pharmaceutically active ingredient after redispersion of the solid dosage form in aqueous media is equivalent to the particle size of the at least one pharmaceutically active ingredient after step (a) but prior to step (b). In a more preferred embodiment, the particle size is equivalent after storage at 25° C. and 60% relative humidity for at least six months.

BRIEF DESCRIPTION OF THE FIGURES

FIG. 1A relates to lyophilized powders. FIG. 1B relates to spray dried powders.

FIG. 5A relates to lyophilized powders. FIG. 5B relates to spray dried powders.

FIGS. 7A and 7B are powder x-ray diffraction patterns for (7A) lyophilized and (7B) spray dried solids containing different amounts of probucol ((a) pure probucol, (b) formulation 3, (c) formulation 2, and (d) formulation 1).

FIGS. 8A and 8B are powder x-ray diffraction patterns for (8A) lyophilized and (8B) spray dried solids containing different amounts of danazol ((a) pure danazol, (b) formulation 6, (c) formulation 5, and (d) formulation 4).

FIGS. 11A, 11B, and 11C are transmission electron microscopy images of (11A) probucol original nanosuspension, (11B) redispersed nanosuspension stabilized using sugar fatty acid ester, and (11C) redispersed suspension stabilized with PVP and SLS.

DETAILED DESCRIPTION OF THE INVENTION

Figure 1A:
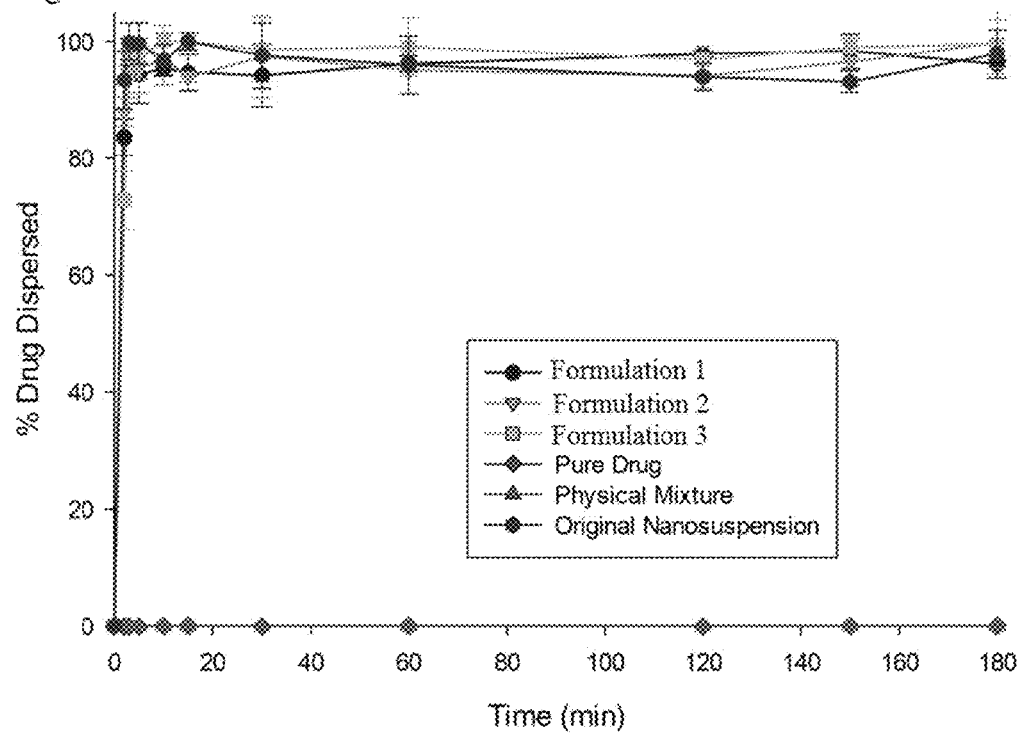
FIGS. 1A and 1B show the results of a dispersion test of dried powders containing probucol as a model drug.

The present invention relates to an efficient solid dosage form containing a sugar ester nanoparticle stabilizer and nanoparticles of at least one pharmaceutically active ingredient. The present invention also relates to a method for preparing such a dosage form without the need to incorporate any additional excipients for stabilizing the nanoparticles, i.e., in the absence of any additional stabilizing excipients. In particular, sugar ester nanoparticle stabilizers stabilize the nanoparticles and prevent agglomeration during particle size reduction and during conversion from nanosuspension to dry solid. In addition, sugar ester nanoparticle stabilizers allow for, upon mixing of the solid dosage form with aqueous media, redispersion into the particle size of the original nanoparticle size of the at least one pharmaceutically active ingredient in the nanosuspension.

Specifically, the present invention is directed to a method of preparing a solid dosage form containing nanoparticles, the method comprising the steps of: (a) reducing particle size of at least one pharmaceutically active ingredient dispersed in a solution containing a sugar ester nanoparticle stabilizer to form a nanosuspension; and (b) drying the nanosuspension of step (a) to form the solid dosage form. The present invention is also directed to a solid dosage form containing nanoparticles prepared by said method.

As used herein, the term "solid dosage form" includes, without limitation, a unit-dose pharmaceutical product that exhibits solid-state physical properties upon storage; "solid dosage form" also simply refers to the dry solid or dry solids that result when the nanosuspension of step (a) is dried in step (b). As used herein, the term "oral solid dosage form" includes, without limitation, a unit-dose pharmaceutical product that exhibits solid-state physical properties upon storage that is administered to patients by way of the mouth. The solid dosage form of the present invention may be used, without further processing, as an oral solid dosage form or it may be further processed, with or without the addition of other excipients, carriers, etc., so as to be incorporated into an oral solid dosage form, e.g., placed into a capsule, compressed into a tablet, encapsulated in a sachet, etc., or incorporated into some other type of dosage form, e.g., (i) powder for inhalation dosage form or aerosol, (ii) powder, granule or lyophilized cake for conversion into parenteral solution or suspension, (iii) powder, granule or other solid materials for conversion into liquid dosage forms, (iv) powder, granules, minitablets, etc., for mixing with or sprinkling on foods, and so forth. As used herein, the term "nanoparticles" or "nanoparticulate" refers to preferably to particles having a size in the range of a few nanometers to 1000 nm, and, more preferably, the average particle size ranges from a few nanometers to 500 nm. In a preferred embodiment of the present invention, the solid dosage form exhibits fast disintegration. As used herein, "fast disintegration" refers to the dispersion of >90% solid dosage form in the dispersion medium within 15 minutes and resulting in a nanosuspension similar to that of the original nanosuspension, i.e., having an equivalent particle size as defined below. In addition to "fast disintegration" dosage forms, the solid dosage forms of the invention may be used to formulate a variety of pharmaceutical dosage forms having a variety of release characteristics, i.e., standard release, modified release, delayed release, extended release, etc.

In the first step of the present inventive method, the particle size of at least one pharmaceutically active ingredient dispersed in a solution containing a sugar ester nanoparticle stabilizer is reduced to form a nanosuspension. This step, and indeed the entire method, is preferably accomplished without the incorporation of any additional excipients for the purpose of stabilizing the nanoparticles, i.e., in the absence of any other nanoparticle stabilizer.

As used herein, "pharmaceutically active ingredient" refers to a drug or drug product that may be used in the diagnosis, cure, mitigation, treatment, or prevention of disease. Any pharmaceutically active ingredient may be used for purposes of the present invention, including both those that are water-soluble and those that are poorly soluble in water. Particularly, the present invention may be used to formulate pharmaceutically active ingredients with poor water solubility. As used herein, a "poorly water soluble" drug refers to a drug substance that is considered to be not "highly soluble." As used herein, a drug is considered "highly soluble" when the highest dose strength is soluble in 250 mL or less of aqueous media over the pH range of 1.0-7.5.

Suitable pharmaceutically active ingredients include, without limitation, nonsteroidal anti-inflammatory drugs, analgesics, 5-alpha-reductase inhibitors, 5-aminosalicylates, 5HT3 receptor antagonists, steroids, bronchodilators, aldosterone receptor antagonists, alkylating agents, alpha glucosidase inhibitors, amoebicides, aminoglycosides, androgens and anabolic steroids, angiotensin converting enzyme (ACE) inhibitors, angiotensin II inhibitors, anorexiants, antacids, anthelmintics, anti-infectives, anti-adrenergic agents, anti-anginal agents, anti-arrhythmics, antibiotics, anti-cholinergics, anti-coagulants, anti-convulsants, anti-depressants, anti-diabetic agents, anti-diarrheals, anti-fungals, anti-gout agents, anti-histamines, anti-hyperlipidemic agents, anti-hyperuricemic agents, anti-malarial agents, anti-metabolites, anti-migraine agents, anti-parkinson agents, anti-platelet agents, anti-bacterials, anti-psoriatics, anti-psychotics, antirheumatics, antiseptic and germicides, anti-viral agents, anxiolytics, sedatives, and hypnotics, anti-convulsants, beta-adrenergic blocking agents, bile acid sequestrants, bisphosphonates, bronchodilators, calcium channel blocking agents, carbonic anhydrase inhibitors, cephalosporins, chelating agents, chemokine receptor agonists, chemokine receptor antagonists, chloride channel activators, cholesterol absorption inhibitors, cholesterol lowering agents, cholinergic agonists, cholinesterase inhibitors, contraceptives, cox-2 inhibitors, decongestants, dipeptidyl peptidase 4 inhibitors, diuretics, dopaminergic agents, gamma-aminobutyric acid analogs, gamma-aminobutyric acid reuptake inhibitors, gastrointestinal agents, anesthetics and other pain-modulating agents, glycoprotein platelet inhibitors, *H. pylori* eradication agents, histamine receptor antagonists, hormones, immunologic agents, immunosuppressive agents, impotence agents, incretin mimetics, inotropic agents, ketolides, laxatives, leukotriene modifiers, meglitinides, metabolic agents, methylanthines, mineralocorticoids, monoamine oxidase inhibitors, muscle relaxants, neuraminidase inhibitors, neuromuscular blocking agents, norepinephrine reuptake inhibitors, norepinephrine-dopamine reuptake inhibitors, nucleoside reverse transcriptase inhibitors (NRTIs), non-nucleoside reverse transcriptase inhibitors (NNRTIs), penicillins, peripheral opioid receptor antagonists, peripheral vasodilators, peripherally acting anti-obesity agents, prolactin inhibitors, protease inhibitors, proton pump inhibitors, psychotherapeutic agents, renin inhibitors, selective serotonin reuptake inhibitors, serotonin-norepinephrine reuptake inhibitors, serotoninergic neuroenteric modulators, statins, thrombin inhibitors, thrombolytics, thyroid drugs, tumor necrosis factor (TNF) inhibitors, tyrosine kinase inhibitors, vasodilators, vasopressin antagonists, vitamins, anti-epileptics, anti-hypertensive agents, anti-muscarinic agents, anti-neoplastic agents, anti-protozoal agents, anti rheumatics, anti-thyroid agents, neuroleptics, cardiac inotropic agents, cough suppressants, cytotoxics, enzymes, lipid regulating agents, nitrates, nutritional agents and combinations thereof. A description of the marketed pharmaceutical active ingredients that fall into these classes of drugs can be found in Martindale; The Complete Drug Reference (The Pharmaceutical Press, 37th Ed., 2011), the disclosure of which is hereby incorporated by reference in its entirety.

The amount of pharmaceutically active ingredient present in the nanosuspension of step (a) preferably ranges from 0.1 to 50% w/w, and more preferably ranges from 1 to 25% w/w, and even more preferably ranges from 1 to 15% w/w. The amount of pharmaceutically active ingredient in the nanosuspension of step (a) is an amount appropriate to provide a pharmaceutically effective amount in a final dosage form. As used herein, "pharmaceutically effective amount" refers to an amount required to bring about a desired pharmacological effect in diagnosis, cure, mitigation, treatment, or prevention. A person of ordinary skill in the art can readily determine an appropriate pharmaceutically effective amount of a given known pharmaceutically active ingredient.

The solution into which the pharmaceutically active ingredient is dispersed can be prepared by any known means in the art. For example, the sugar ester nanoparticle stabilizer can be added to a suitable solvent. Suitable solvents include, without limitation, water and mixtures of water with organic solvents such as ethanol or isopropanol. It is important to keep in mind that, when using mixtures of water with organic solvent, the amount of organic solvent should be limited such that the sugar ester nanoparticle stabilizer will dissolve and the pharmaceutically active ingredient will not dissolve but rather remain as a suspended solid. The solution is preferably water or an aqueous solution.

The sugar ester nanoparticle stabilizer according to the present invention is preferably a derivative, i.e., a sugar fatty acid ester. As used herein "sugar fatty acid ester" refers to a compound composed of sugar and fatty acids. In a preferred embodiment of the present invention, the sugar fatty acid ester of the present invention is composed of a sugar or sugar derivative esterified with medium chain fatty acids. Suitable sugars include, without limitation, monosaccharides (e.g., glucose, fructose, galactose, and mannose), disaccharides (e.g., sucrose, maltose, and lactose), oligosaccharides (e.g., fructo-oligosaccharide and galacto-saccharide), and sugar derivatives (e.g, erythritol, threitol, arabitol, xylitol, adonitol, fucitol, sorbitol, mannitol, galactitol, inositol, iditol, isomalt, maltitol, volemitol, and lactitol). Suitable medium chain fatty acids include, without limitation, caproic acid, caprylic acid, capric acid, lauric acid, and fatty acids with aliphatic tails of 6 to 12 carbons. The sugar fatty acid esters of a particular sugar can be produced with medium chain fatty acids with different chain lengths, and they can also be mixtures of esters with different fatty acid chain lengths. The sugar ester nanoparticle stabilizer of the present invention may be one or a combination of more than one sugar fatty acid esters.

The amount of sugar ester nanoparticle stabilizer in the nanosuspension is preferably in the range of 1 to 25% w/w and, more preferably, is in the range of 1 to 15% w/w. One of ordinary skill in the art can readily work within the noted ranges to obtain a suitable nanosuspension.

The process used to reduce the particle size of the pharmaceutically active ingredient particles to the nanoparticle range to form the nanosuspension may be any high-energy size reduction process, including, but not limited to, wet milling, homogenization, microfluidization, nanoprecipitation, emulsification and solvent evaporation, supercritical fluid technology, and spray drying. In small scale productions, wet media milling technology is typically used, such as a Turbula® Shaker Mixer (Glen Mills Inc., Clifton, N.J.), in which a milling chamber is loaded with the drug particle suspension and milling media containing milling beads (e.g., zirconium oxide beads). Due to mechanical rotation of the milling chamber and shear forces generated by collision of the milling beads and the suspended particles of the pharmaceutically active ingredients, drug particle size is reduced until the desired nanoparticle size is obtained. Wet milling technology, such as a Dyno® Mill (Glen Mills Inc., Clifton, N.J.) and a Netzsch Mill (Netzsch Inc., Exton, Pa.) can be used for larger scale productions.

In a preferred embodiment of the present invention, wet media milling technology is utilized for particle size reduction. The method is also referred to as the "top-down" method, because large particles are broken down into small nanoparticles. "Nanosuspension of poorly soluble drugs: Preparation and development by wet milling," Int. J. Pharm. 411:215-22 (2011). While this method is preferred, there are also other methods that can be used in conjunction with step (a) of the present invention, e.g., the "bottom-up" method, where nanoparticles are formed by precipitation of drug from solution. Such a precipitation process can form a nanosuspension by itself or the process can also be followed by a high shear milling or further particle size reduction process. "Production methods for nanodrug particles using the bottom-up approach," Adv. Drug Del. Rev. 63(6):406-416 (2011).

In addition to pharmaceutically active ingredient and sugar ester nanoparticle stabilizer, nanosuspensions may contain pharmaceutical excipients, such as pH modifiers, buffering agents, bulking agents, diluents, lubricants, glidants, viscosity modifiers, suspending agents, surfactants, disintegrants, sweeteners, flavoring agents, coloring agents, preservatives, antioxidants, etc., or combinations thereof. A person of ordinary skill in the art can readily determine the type and the appropriate amount of such pharmaceutical excipients if present in the nanosuspension of step (a) and depending on the type of dosage form ultimately desired. Such additional excipients may be added to the solution containing the sugar ester nanoparticle stabilizer before or after the pharmaceutically active ingredient is dispersed therein. Alternatively such additional excipients may be added to the nanosuspension, i.e., after particle size reduction. Additionally, other excipients such as diluents, lubricants, glidants, disintegrants, etc., may be added after step (b) as part of further processing of a solid dosage form.

In the second step of the present inventive method, the nanosuspension of step (a) is subjected to drying to form a solid dosage form. This step is accomplished without the incorporation of any additional excipients for the purpose of stabilizing the nanoparticles and preventing agglomeration. Generally, the transformation of nanosuspension into dry solids can be achieved by any known process such as freeze drying, lyophilization, spray drying, spray granulation, fluid bed process/bead layering, spray-freeze drying, tray drying, vacuum drying, or combination thereof. As discussed above, it is well recognized in the field that the transformation of nanosuspensions into dry solids includes the challenges of agglomeration of the nanoparticles. In addition, challenges facing preparation of the solid dosage form include the issue of redispersibility of the dry solids to the original nanoparticle sizes.

The present inventors have found that, surprisingly, sugar esters, more preferably sugar fatty acid esters as defined above, can serve as nanoparticle stabilizers during particle size reduction, prevent agglomeration during drying, and allow for redispersion of the dry solids to original nanoparticle size of the original nanosuspension. Indeed the present inventors have unexpectedly found that sugar esters can be used to formulate solid dosage forms without the use of significant amounts of additional excipients that typically limit drug loading content.

Sugar fatty acid esters are non-ionic surfactants available in a wide range of HLB values depending upon the chain length and the number of fatty acid groups. Sugar fatty acid esters are safe and biodegradable and are prepared by esterification of natural derived chemicals, such as sugars and fatty acids. They are non-toxic, have an extremely low order of irritation, and are widely used in the food, cosmetic, and pharmaceutical industries. Sugar fatty acid esters are also used in various vesicle drug delivery systems, for the preparation of microspheres, and as emulsifiers for nano-systems such as nanoemulsions, solid-lipid nanoparticles, and nanodispersions. The use of sugar fatty acid esters also includes solid-in-oil nanosuspensions for transdermal delivery and transcutaneous protein delivery. However, despite the use of sugar fatty acid esters in the pharmaceutical field, the present inventors are not aware of any studies or disclosures in the field regarding the use of sugar fatty acid esters as nanoparticle stabilizers for prevention of agglomeration and for redispersibility of dry solids.

Indeed, the present inventors have found that sugar fatty acid esters serve to prevent agglomeration of the nanoparticles during preparation of the nanosuspension, during drying for conversion to dry solids, and allow for redispersion into the particle size of the original nanosuspension without the need for any additional stabilizer excipients and/or sonication. Surprisingly, with regard to redispersibility of the dry solids, the present inventors have found that the redispersed nanoparticles are equivalent to the particle size of the original nanosuspension. As used herein, "equivalent" refers to median particle size that remains preferably within 50% of the original particle size and more preferably within 25% of the original particle size.

Without wishing to be bound by theory, it is believed that the sugar fatty acid esters serve as nanoparticle stabilizers due to their binding mechanism to the drug molecules. One possible interaction contributing to the nanoparticle stabilization is the hydrophobic bonding (similar to Van der Waals interactions). In the presence of water, a hydrophobic bond can be formed between the non-polar side groups of the drug molecule and sugar fatty acid ester. As a result, the hydrophilic sugar component of the sugar ester molecule becomes localized on the surface of the drug molecule. Other possible interactions responsible for the nanoparticle stabilization include the hydrophilic bonding and forming of hydrogen bonds between the polar groups of the drug molecule and the hydrophilic portion of the sugar fatty acid ester.

In addition, several mechanisms via lyoprotection of nanoparticles during lyophilization and use of dispersants during spray drying might contribute to nanoparticle stabilization by the sugar fatty acid ester. Such mechanisms include formation of an amorphous glassy state, water replacement by excipients, and hydrogen bonding between excipients and nanoparticles. One or a combination of these mechanisms might be responsible for the stabilization of nanoparticles with the sugar fatty acid ester during drying or redispersion of the dry solids to original nanoparticle size. Specifically, immobilization of nanoparticles within a glassy matrix of the sugar ester can prevent their aggregation and protect them against the mechanical stresses of ice crystals. With regard to water replacement, it is possible that the formation of hydrogen bonds between drug particles and lyoprotectants protects the nanoparticles by serving as water substitutes. As discussed above, the hydrogen bonding between sugar esters and drug particles might be responsible for stabilization of nanoparticles during the drying process and prevention of agglomeration. This hydrogen bonding might be the reason why sugar esters are superior to conventional nanoparticle stabilizers. In particular, for example, sucrose laurate is a monoester with a molecular weight of 525. However, conventional nanoparticle stabilizers have a large molecular weight compared to, for example, sucrose laurate. Accordingly, it is possible that interaction of these large molecules would limit interaction on the drug particle surface due to structural hindrance as compared to sugar fatty acid esters. Other reasons conventional nanoparticle stabilizers may not perform as well as sugar fatty acid esters include polymer chain entanglement or particle fusion. In this regard, for example, sucrose laurate is a non-ionic surfactant that is more effective than conventional nanoparticle stabilizers such as PVA, PVP, and poloxamer 188. Indeed, sugar fatty acid esters may offer advantages over conventional polymeric stabilizers due to higher adsorption potential.

The present inventors have also found that, unexpectedly, the stabilization properties of the sugar ester nanoparticle stabilizers are unaffected after storage of the solid dosage forms for at least 6 months at 25° C. and 60% relative humidity. Indeed, the solid dosage forms demonstrated no significant changes in redispersibiltiy, i.e., particle size, even after storage for 6 months at 25° C. and 60% relative humidity.

Specific embodiments of the invention will now be demonstrated by reference to the following examples. It should be understood that these examples are disclosed by way of illustrating the invention and should not be taken in any way to limit the scope of the present invention.

Redispersibility Study

COMPARATIVE EXAMPLES

With reference to Table 1, solid dosage forms comprising active ingredients and nanoparticle stabilizers commonly used in the art were prepared. For each solid dosage form, an aqueous suspension of active ingredient and nanoparticle stabilizer were prepared in accordance with the amounts indicated in Table 1. Danazol used in this example and all other examples in the present disclosure was donated by a major generic pharmaceutical company based in the United States. Probucol used in this example and all other examples in the present disclosure were purchased from Sigma Aldrich (St. Louis, Mo.). The aqueous solutions were subsequently milled via a Turbula® Shaker Mixer with milling media containing zirconium oxide beads for four hours at 90 rpm. The particle size of each resultant nanosuspension was measured via a DelsaNano C particle size analyzer using a dynamic light scattering technique at 25° C. Subsequently, each resultant nanosuspension was subjected to drying using lyophilization and spray drying techniques to form dry powders. The dry powders were then tested for redispersibility through redispersion in water with gentle shaking followed by analysis for particle size measurement via the DelsaNano C particle size analyzer.

TABLE 1

| Drug + Stabilizer | Particle size of nanosuspension | Particle size of redispersed dry powder in water |
|---|---|---|
| 0.500 g of danazol + 10 or 15 mL of (0.1% Sodium lauryl sulfate (SLS) and 0.5% polyvinyl pyrollidone) | 204 nm | 600 nm (d90 >2.2 μm) |
| 0.500 g of danazol + 0.250 g of poloxamer 188 | 203 nm | No redispersion |
| 0.500 g of danazol + 0.500 g polyvinyl pyrollidon (Kollidon ® 30) | 500 nm | No redispersion |
| 0.500 g of danazol + 0.500 g of hydroxyl propyl methyl cellulose (HPMC) | 342 nm | 1.3 μm ($d_{90}$ = 7.6 μm) |
| 0.500 g of danazol + 0.500 g/0.750 g POE Cetyl/Stearyl Ether (Eumulgin ® B2) | ≈427 nm | >1 μm |
| 0.500 g of danazol + 0.500 g of macrogol cetostearyl ether 12 (Kolliphor CS 12) | 234 nm | No redispersion |
| 0.500 g of danazol + 0.500 g of Eumulgin ® B2 + 10 mg SLS | 439 nm | No redispersion |

TABLE 1-continued

| Drug + Stabilizer | Particle size of nanosuspension | Particle size of redispersed dry powder in water |
|---|---|---|
| 0.500 g of danazol + 0.500 g of Eumulgin ® B2 + 10 mg glycine | 269 nm | 1.4 μm |
| 0.500 g of danazol + 0.500 g of Eumulgin ® B2 + 10 mg betaine | 247 nm | 5.5 μm |
| 0.500 g of danazol + 1:1 of Eumulgin ® B2:Kolliphor ® CS 12 | 257 nm | 990 nm |
| 0.500 g of probucol + 10 mL of (0.1% Sodium lauryl sulfate (SLS) and 0.5% polyvinyl pyrollidon) | 273 nm | 1.8 μm ($d_{90}$ = 5.5 μm) |

As seen in Table 1, nanoparticle stabilizers commonly used in the art were unable to demonstrate redispersion to the particle size of the original nanosuspension upon dispersion of the powders in aqueous media. Instead, nanoparticle stabilizers commonly used in the art either demonstrated no redispersibility of the active ingredients or demonstrated redispersibility with much higher particle sizes, generally in the micron range. Similar results were observed when the powders were redispersed in an aqueous media comprising HCl and SLS at a pH of 6.8. Sucrose palmitate, sucrose stearate and their combinations were also tested as stabilizers, and none of them produced nanosuspensions. Therefore, they were not dried and were not subjected to redispersion test.

Example 1

With reference to Table 2, solid dosage forms of Formulations 1-3 comprising the active ingredient probucol and sucrose laurate as stabilizer were prepared. For each of Formulations 1-3, aqueous solutions of sucrose laurate were prepared and probucol was suspended in them in accordance with the amounts indicated in Table 2. The aqueous suspensions were subsequently milled via a Turbula® Shaker Mixer with milling media containing zirconium oxide beads for four hours at 90 rpm. The particle size of each of the resultant nanosuspensions for Formulations 1-3 was measured via a DelsaNano C particle size analyzer using a dynamic light scattering technique at 25° C. Subsequently, each resultant nanosuspension of Formulation 1-3 was subjected to vacuum drying, lyophilization, and spray drying to form dry powders. The dry powders were then tested for redispersibility through redispersion in water with gently shaking followed by analysis for particle size measurement via the Del saNano C particle size analyzer.

As seen in Table 2, the present inventors have found that sugar esters are able to restore the particle size of the active ingredients to the original nanoparticle size upon redispersion of the powders in aqueous media without the use of any additional excipients. In other words, the present invention demonstrates that the particle size of the active ingredients after redispersion of the powders is equivalent to the particle size of the original nanosuspension.

With reference to Table 3, the powders from formulations 1 and 3 in Table 2 were also tested regarding redispersibility in various simulated biological fluids. The redispersion of formulation 2 was not studied as concentrations of drug and stabilizer in this formulation was intermediate between those in formulations 1 and 3 and it was assumed that its redispersibility would be similar to that of the other two formulations. When the spray dried or lyophilized powders stabilized with sucrose laurate were redispersed in low pH solutions, such as 0.1 M HCl (pH of 1.2) and 0.01 M HCl (pH of 2), aggregation of nanoparticles was observed as the dry nanoparticles were not able to redisperse to the particle size of the original nanosuspension. However, the addition of 2% sodium lauryl sulfate ("SLS") with these dried powders led to redispersion to particle size of the original nanosuspension. Gastrointestinal fluid contains surfactants including SLS, so the addition of SLS replicates redispersion in gastrointestinal conditions.

TABLE 2

| Formulation | Compositions | Original Nanosuspension (nm) | Particle size of redispersed vacuum dried solids (nm) in water | Particle size of redispersed lyophilized solids (nm) in water | Particle size of redispersed spray dried solids (nm) in water |
|---|---|---|---|---|---|
| 1 | 0.500 g drug + 0.150 g of sucrose laurate | 173 | 179 | 173 | 183 |
| 2 | 0.750 g drug + 0.250 g of sucrose laurate | 190 | 189 | 189 | 184 |
| 3 | 1.000 g drug + 0.250 g of sucrose laurate | 198 | 193 | 174 | 206 |

TABLE 3

| Formulation | Compositions | Original Nanosuspension (nm) | Particle size of redispersed in aqueous system (nm) | Particle size of redispersed in 0.01N HCL (nm) | Particle size of redispersed in pH 6.8 (nm) | Particle size of redispersed in 0.01N HCL with 2% SLS (nm) |
|---|---|---|---|---|---|---|
| 1 | 0.500 g drug + 0.150 g of sucrose laurate | 173 | 179 | Agglomeration | 181 | 174 |
| 3 | 1.000 g drug + 0.250 g of sucrose laurate | 198 | 193 | Agglomeration | 177 | 204 |

Example 2

With reference to Table 4, solid dosage forms of Formulations 4-6 comprising the active ingredient danazol and sucrose laurate as stabilizer were prepared. For each of Formulations 4-6, aqueous suspensions of danazol in aqueous sucrose laurate solutions were prepared in accordance with the amounts indicated in Table 4. The aqueous suspensions were subsequently milled via a Turbula® Shaker Mixer with milling media containing zirconium oxide beads for four hours at 90 rpm. The particle size of each of the resultant nanosuspensions for Formulations 4-6 was measured via a DelsaNano C particle size analyzer using a dynamic light scattering technique at 25° C. Subsequently, each resultant nanosuspension of Formulations 4-6 was subjected to vacuum drying, lyophilization, and spray drying to form dry powders. The dry powders were then tested for redispersibility through redispersion in water with gently shaking followed by analysis for particle size measurement via the Del saNano C particle size analyzer.

TABLE 4

| Formulation | Compositions | Original Nanosuspension (nm) | Particle size of redispersed vacuum dried solids (nm) in water | Particle size of redispersed lyophilized solids (nm) in water | Particle size of redispersed spray dried solids (nm) in water |
|---|---|---|---|---|---|
| 4 | 0.500 g drug + 0.375 g of sucrose laurate | 239 | 316 | 231 | 250 |
| 5 | 0.750 g drug + 0.500 g of sucrose laurate | 239 | 243 | 245 | 241 |
| 6 | 1.000 g drug + 0.500 g of sucrose laurate | 253 | 234 | 265 | 265 |

As seen in Table 4, the present inventors have found that sugar esters are able to restore the particle size of a different active ingredient to the original nanoparticle size upon redispersion of the powders in aqueous media without the use of any additional excipients. In other words, the present invention demonstrates that the particle size of the active ingredients after redispersion of the powders is equivalent to the particle size of the original nanosuspension.

Example 3

With reference to Table 5, solid dosage forms of Formulations 7 and 8 comprising the active ingredient fenofibrate and sucrose laurate as stabilizer were prepared. For each of Formulations 7 and 8, aqueous solutions sucrose laurate were prepared and fenofibrate was suspended in them in accordance with the amounts indicated in Table 5. The suspensions were subsequently milled via a Turbula® Shaker Mixer with milling media containing zirconium oxide beads for four hours at 90 rpm. The particle size of each of the resultant nanosuspensions for Formulations 7 and 8 was measured via a DelsaNano C particle size analyzer using a dynamic light scattering technique at 25° C. Subsequently, each resultant nanosuspension of Formulations 7 and 8 were subjected to vacuum drying and lyophilization to form oral solid dosage forms. Each prepared oral solid dosage form was then tested for redispersibility through redispersion in water followed by analysis for particle size measurement via the DelsaNano C particle size analyzer.

TABLE 5

| Formulation | Compositions | Original Nanosuspension (nm) | Particle size of redispersed vacuum dried solids (nm) in water | Particle size of redispersed lyophilized solids (nm) in water |
|---|---|---|---|---|
| 7 | 0.500 g drug + 0.250 g of sucrose laurate | 210 | 235 | 196 |

TABLE 5-continued

| Formulation | Compositions | Original Nanosuspension (nm) | Particle size of redispersed vacuum dried solids (nm) in water | Particle size of redispersed lyophilized solids (nm) in water |
|---|---|---|---|---|
| 8 | 1.000 g drug + 0.500 g of sucrose laurate | 209 | 264 | 192 |

As seen in Table 5, the present inventors have found that sugar esters are able to restore the particle size of yet another active ingredient to the original nanoparticle size upon redispersion of the dosage forms in aqueous media without the use of any additional excipients. In other words, the present invention demonstrates that the particle size of the active ingredients after redispersion of the dosage forms is equivalent to the particle size of the original nanosuspension.

Example 4

With reference to Table 6, solid dosage forms of Formulations 9 and 10 comprising active ingredients and sucrose laurate as stabilizer were prepared. Specifically, oral solid dosage forms of Formulation 9 comprise a weakly acidic drug, and oral solid dosage forms of Formulation 10 comprise a weakly basic drug. More specifically, for dosage forms of Formulation 9, aqueous suspensions containing 0.5 g mefenamic acid and 0.5 g sucrose laurate were prepared. For dosage forms of Formulation 10, aqueous suspensions of 0.5 g itraconazole and 0.5 g sucrose laurate were prepared. These aqueous suspensions were subsequently milled via a Turbula® Shaker Mixer for four hours at 90 rpm. The particle size of the resultant nanosuspensions of Formulations 9 and 10 were measured via a DelsaNano C particle size analyzer using a dynamic light scattering technique at 25° C. The nanosuspensions of Formulation 9 were then subjected to lyophilization to form oral solid dosage forms. Similarly, the resultant nansuspensions of Formulation 10 were subjected to lyophilization to form oral solid dosage forms. Each prepared oral solid dosage form was then redispersed in water with gentle shaking and subsequently analyzed for particle size measurement via the DelsaNano C particle size analyzer.

TABLE 6

| Formulation | Compositions | Original Nanosuspension (nm) | Particle size of redispersed lyophilized solids (nm) in water |
|---|---|---|---|
| 9 | 0.500 g drug + 0.500 g of sucrose laurate | 288 | 299 |
| 10 | 0.500 g drug + 0.500 g of sucrose laurate | 225 | 251 |

As seen in Table 6, the present inventors have found that sugar esters are able to restore the particle size of weakly acidic and weakly basic drugs to the original nanoparticle size upon redispersion of the dosage forms in aqueous media without the use of any additional excipients. In other words, the present invention demonstrates that the particle size of the active ingredients after redispersion of the dosage forms is equivalent to the particle size of the original nanosuspension.

Example 5

With reference to Table 7, solid dosage forms of Formulations 11-13 comprising the active ingredient probucol and lactose laurate as stabilizer were prepared. For each of Formulations 11-13, aqueous suspensions of probucol in lactose laurate aqueous solutions were prepared in accordance with the amounts indicated in Table 7. The suspensions were subsequently milled via a Turbula® Shaker Mixer with milling media containing zirconium oxide beads for four hours at 90 rpm. The particle size of each of the resultant nanosuspensions for Formulations 11-13 was measured via a DelsaNano C particle size analyzer using a dynamic light scattering technique at 25° C. Subsequently, each resultant nanosuspension of Formulations 11-13 was subjected to vacuum drying and lyophilization to form oral solid dosage forms. Each prepared oral solid dosage form was then tested for redispersibility through redispersion in water followed by analysis for particle size measurement via the Del saNano C particle size analyzer.

TABLE 7

| Formulations | Compositions | Particle size (nm) (nanosuspension) | Particle size (nm) (vacuum dried and redispersed) | Particle size (nm) (lyophilized and redispersed) |
|---|---|---|---|---|
| 11 | 0.500 g drug + 0.075 g lactose laurate | 207 | 209 | 177 |
| 12 | 1.000 g drug + 0.075 g lactose laurate | 222 | — | 241 |
| 13 | 1.000 g drug + 0.150 g lactose laurate | 171 | 186 | 183 |

As seen in Table 7, the present inventors have found that sugar esters are able to restore the particle size of active ingredients to the original nanoparticle size upon redispersion of the dosage forms in aqueous media without the use of any additional excipients. In other words, the present invention demonstrates that the particle size of the active ingredients after redispersion of the dosage forms is equivalent to the particle size of the original nanosuspension.

Dispersion Study

With reference to FIGS. 1A, 1B, 2, 3 and 4, solid dosage forms comprising the active ingredient probucol and sucrose laurate as nanoparticle stabilizer were tested with regard to dispersion rate as compared to probucol itself, a physical mixture (containing probucol, sucrose laurate, and SLS), and solid dosage forms comprising the active ingredient probucol and nanoparticle stabilizers commonly used in the art.

Solid dosage forms of formulations 1, 2 and 3 of probucol, each including sucrose laurate, were prepared via milling by Turbula® Shaker Mixer for four hours and subsequent drying to form lyophilized powder. Dispersion tests were then run on each of the dosage forms using USP apparatus II (the paddle method). Dried samples corresponding to 20 mg of the lyophilized powder were weighed and mixed with 2% SLS and placed into 250 mL of dissolution media with a holding temperature at 37±0.5° C. The rotation speed of the paddle was set to 50 rpm. The dispersion test was performed in two steps: stimulated gastric fluid (pH 1.2) for up to 120 minutes, and changing the pH to pH 6.8 after that by adding 1N NaOH. This is to mimic the gastrointestinal pH conditions. Aliquots of the suspension were taken after 1, 3, 5, 10, 15, 30, 60, 120, 150, and 180 minutes. The aliquots were then filtered through a hydrophilic PTFE membrane filter with 0.45 µm pore size, diluted appropriately with an organic solvent to dissolve drug particles and analyzed for drug content by HPLC.

Figure 1B:
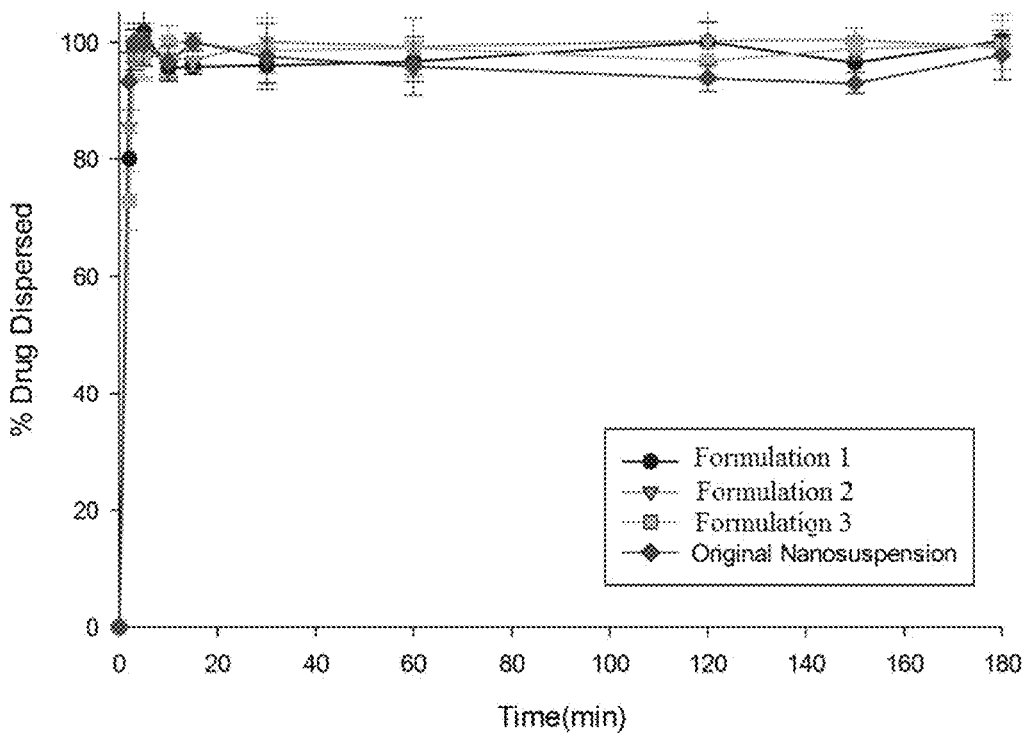
Figure 2:
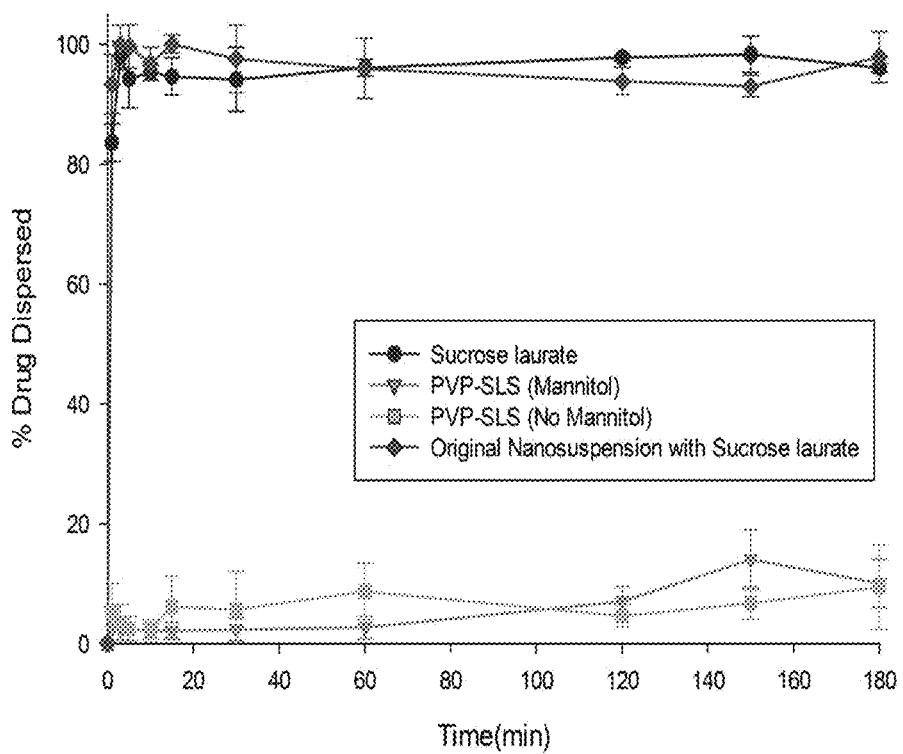
FIG. 2 shows a comparison of lyophilized powders containing probucol with sucrose laurate, PVP-SLS-No Mannitol, PVP-SLS-Mannitol and original nanosuspension.

As seen in FIGS. 1A and 1B, the lyophilized powders demonstrated 95% dispersion of the drug nanoparticles within 3-5 minutes and the particle size of the redispersed powder was observed to be similar to that of the original nanosuspension size. In comparison, as seen in FIG. 1A, the neat probucol powder and the physical mixture did not demonstrate any drug dispersion as the large drug particles were filtered out by the 0.45 µm pore size filter. In addition, with reference to FIG. 2, lyophilized powders containing probucol, PVP-SLS, and no mannitol, as well as lyophilized powders containing probucol, PVP-SLS, and mannitol, had very poor dispersion in comparison.

Figure 3:
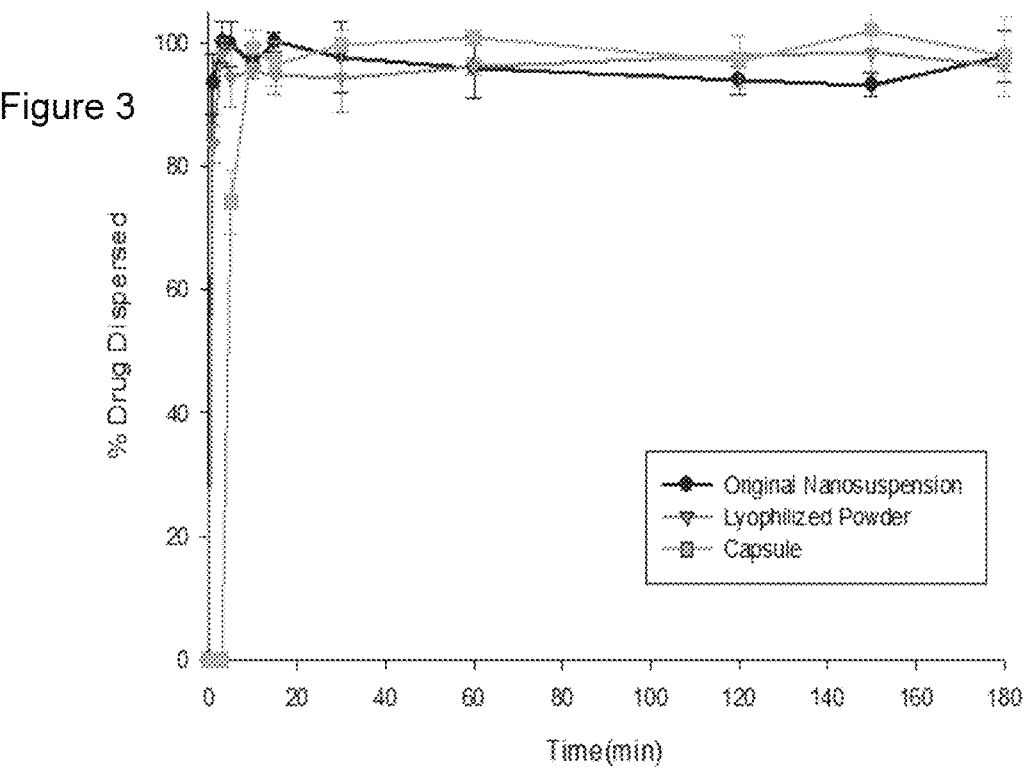
FIG. 3 shows the results of a dispersion test of original nanosuspension, lyophilized powder, and capsule containing probucol as a model drug.
Figure 4:
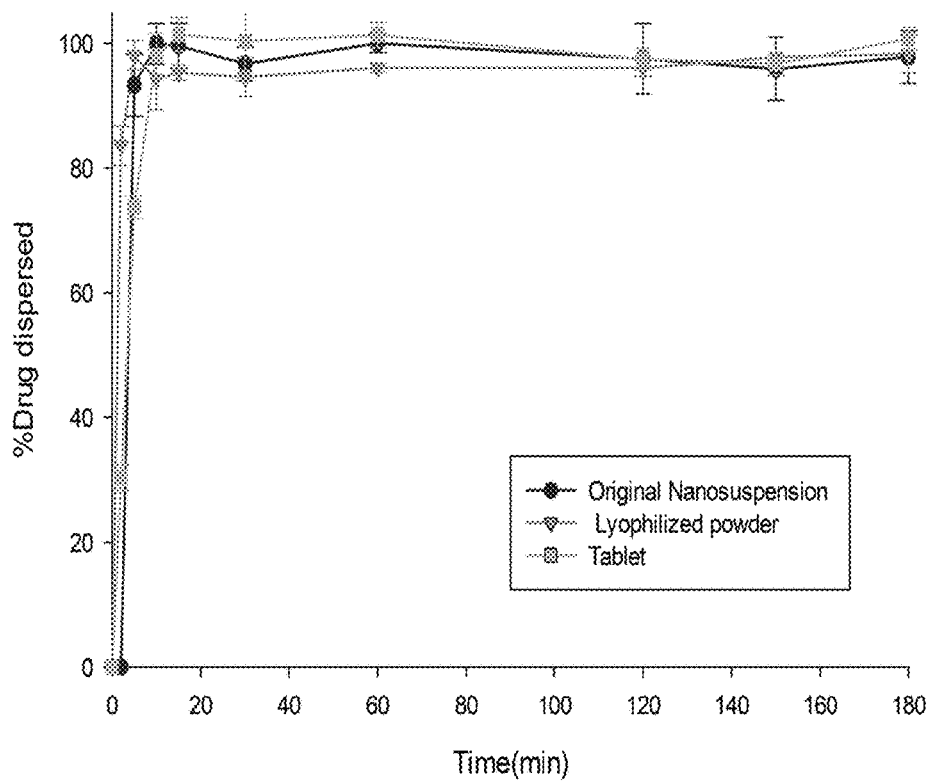
FIG. 4 shows the results of a dispersion test of original nanosuspension, lyophilized powder and tablet containing probucol as a model drug.

Dispersion tests were also performed on capsules and tablets of the lyophilized powder. For capsules, lyophilized samples corresponding to 20 mg of drug were weighted and mixed with 2% SLS and lactose and filled in a size 3 capsule with an average weight of 150 mg. For tablets, lyophilized samples corresponding to 20 mg of drug were weighed and mixed with 2% SLS and 5% Kollidon® CL. Lactose was added as a diluent. Tablets, with the weight of ca. 150 mg each, were compressed at pressures 2.1±0.2 MPa using 8 mm flat face punches on a single punch Carver Press assembly. As seen in FIGS. 3 and 4, the capsules and tablets demonstrated similar dispersion results as the lyophilized powders and original nanosuspension, with 95% dispersion of the drug nanoparticles within 10 minutes.

Figure 5A:
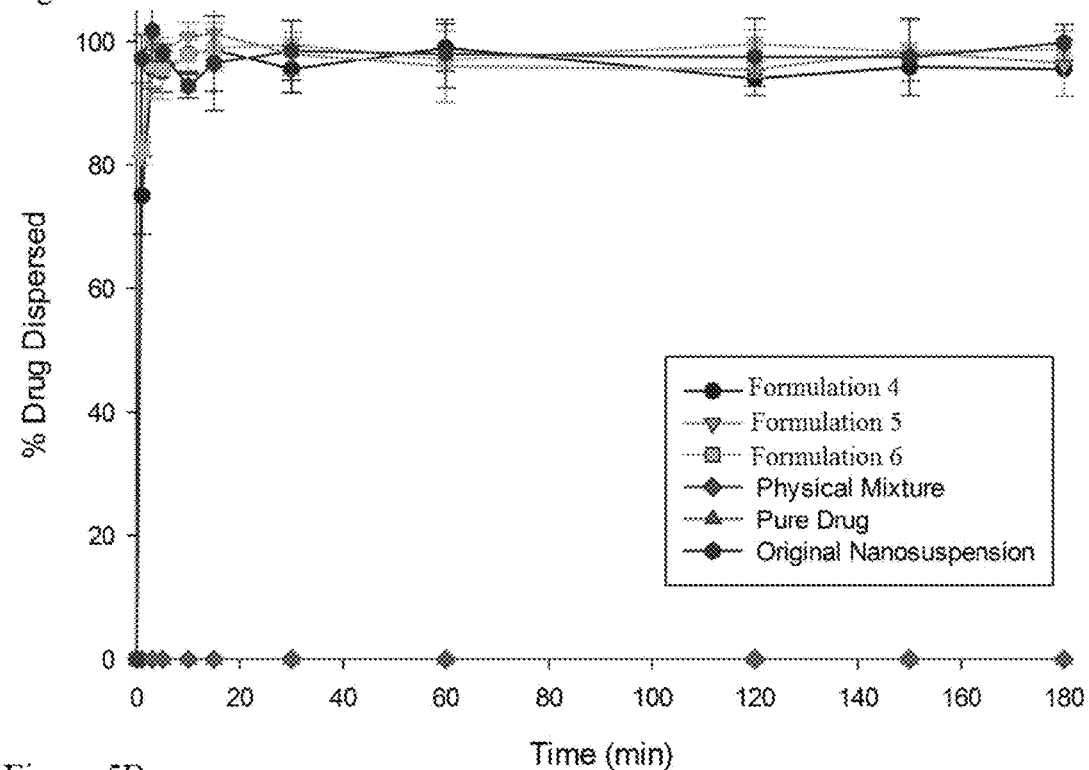
FIGS. 5A and 5B show the results of a dispersion test of dried powders containing danazol as a model drug.
Figure 5B:
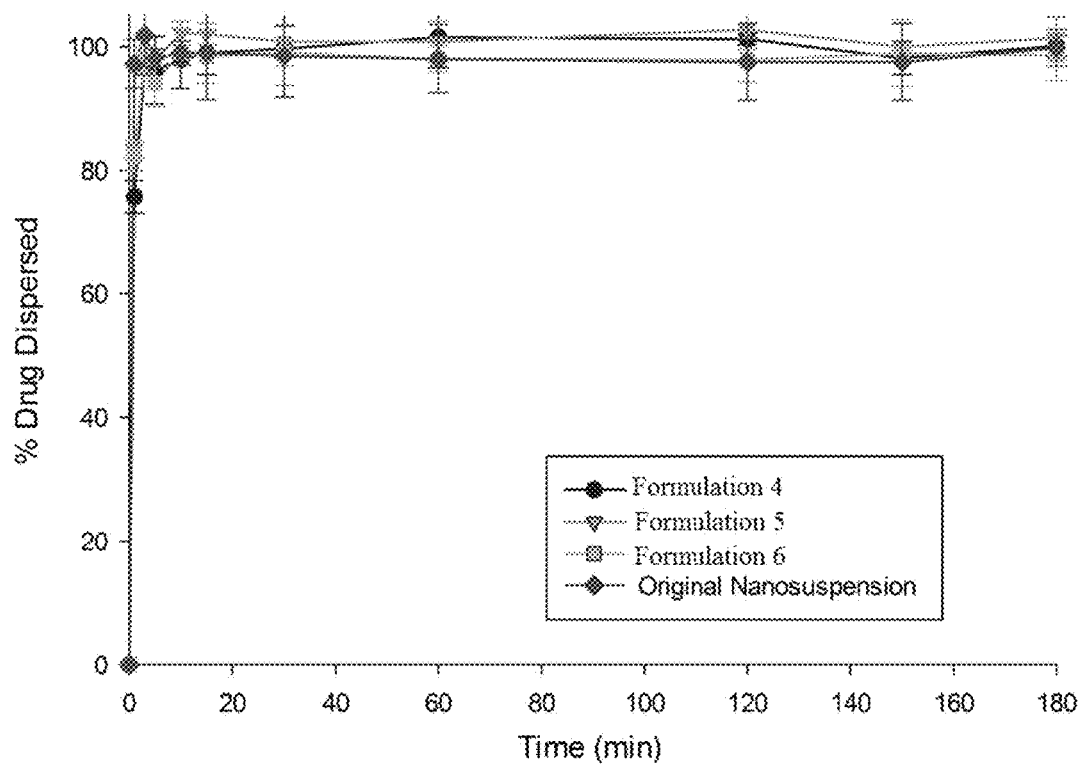
Figure 6:
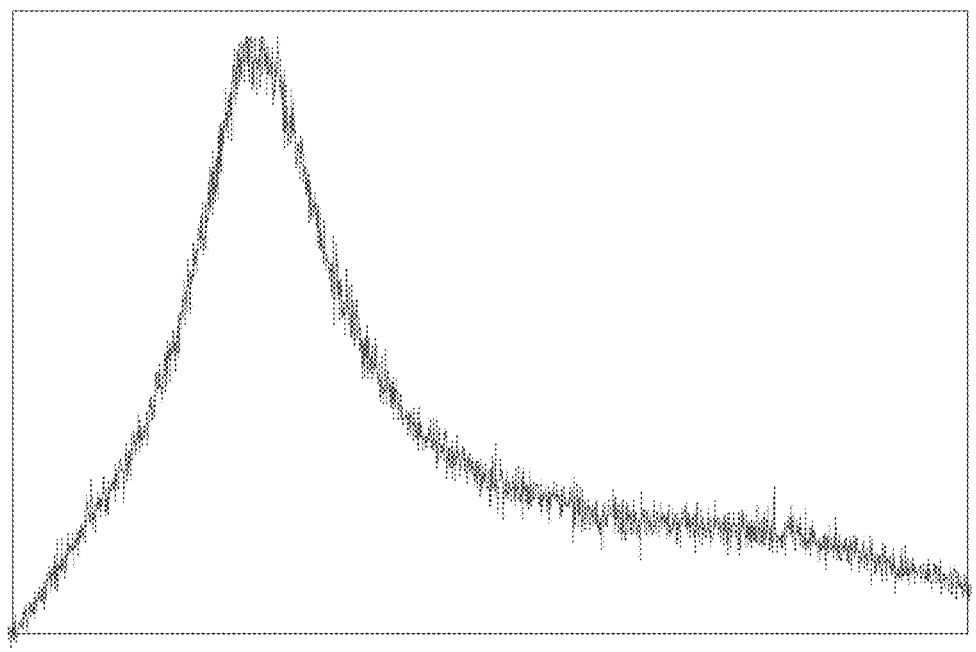
FIG. 6 is a powder x-ray diffraction pattern for sucrose laurate.
Figure 9A:
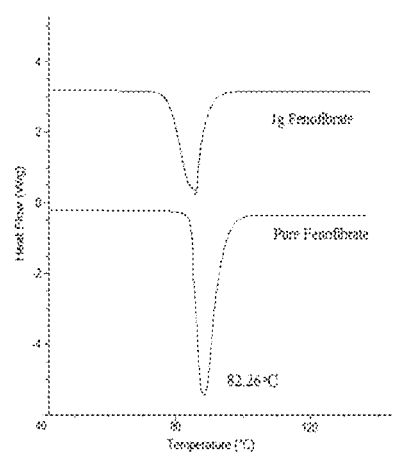
FIGS. 9A and 9B are the differential scanning calorimetry pattern (9A) and powder x-ray diffraction pattern (9B) for lyophilized powder containing fenofibrate.
Figure 9B:
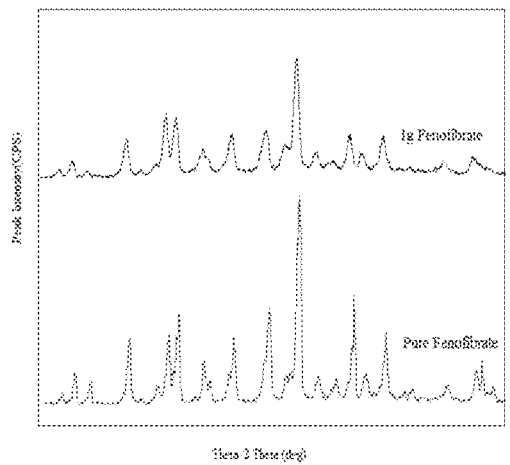
Figure 10:
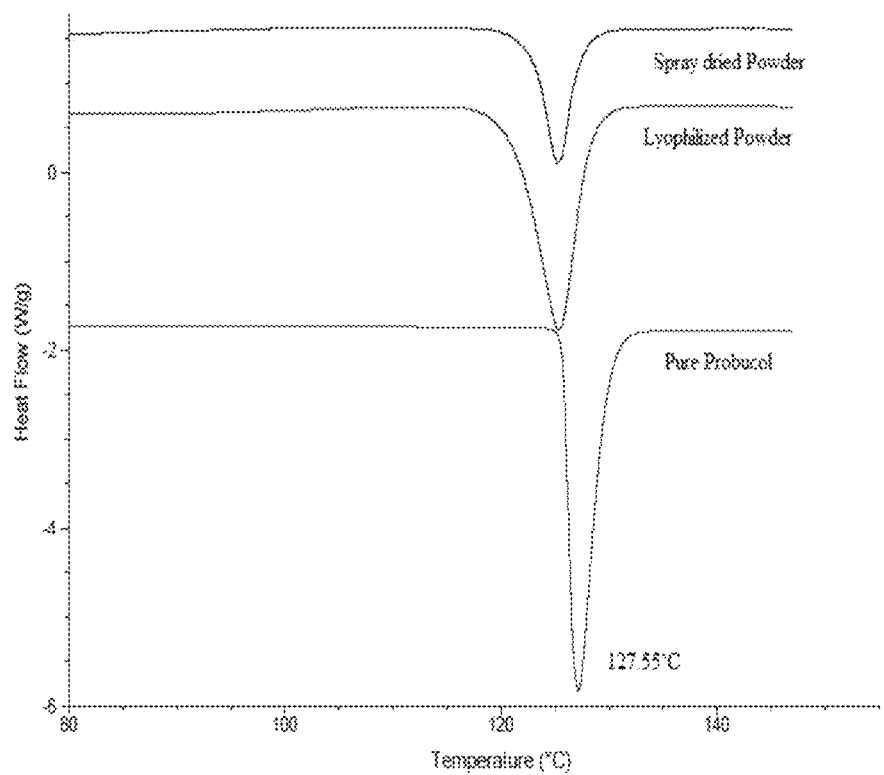
FIG. 10 shows a differential scanning calorimetry study of pure probucol, lyophilized powder and spray dried powder.

With reference to FIGS. 5A and 5B, similar dispersion tests were run with lyophilized and spray dried powders of solid dosage forms containing danazol and sucrose laurate with similar results.

Physico-Chemical and Morphology Study

With regard to wet media milling, a concern is always present with regard to conversion of crystalline drugs into amorphous forms due to the generation of energy during the milling process. For preparation of solid dosage forms, it is essential that the nanoparticles remain in crystalline form and do not convert into amorphous forms. As seen in FIGS. 6, 7A, 7B, 8A, 8B, 9A, 9B, and 10, the examples of the present invention disclosed herein showed that the nanoparticles remained in crystalline form and did not convert to amorphous forms upon analysis via X-ray diffractometry (power XRD) and differential scanning calorimetry techniques (DSC).

With reference to FIGS. 11A, 11B, and 11C, the morphology of examples of the present invention was also analyzed via Transmission Electron Microscopy (TEM). This figure represents the TEM image of the original probucol nanosuspension, redispersed nanosuspension containing sugar fatty acid esters as stabilizer, and redispersed nanosuspension containing PVP-SLS as stabilizers. As seen in this figure, dry powder containing sugar fatty acid esters easily redispersed into the particle size of the original nanosuspension. However, the dry powder containing PVP-SLS could not redisperse into the particle size of the original nanosuspension and had particle size of greater than 1 micrometer.

Stability Study

Example 6

With reference to Table 8, solid dosage forms comprising active ingredients and sucrose laurate as nanoparticle stabilizer were prepared. Specifically, these oral solid dosage forms were tested with regard to their redisersibility upon storage at appropriate conditions for up to 6 months. For each solid dosage form, an aqueous suspension of active ingredient and sucrose laurate was prepared in accordance with the amounts indicated in Table 8. The aqueous suspensions were subsequently milled via a Turbula® Shaker Mixer with milling media containing zirconium oxide beads for four hours at 90 rpm. Particle size of the resultant nanosuspensions was measured via a DelsaNano C particle size analyzer using a dynamic light scattering technique at 25° C. The nanosuspensions were then subjected to drying via lyophilization and spray drying to form lyophilized powder and spray dried powder, respectively. Each of the dosage forms were subsequently redispersed in water with gentle shaking after 1 day, 3 months, and 6 months of storage time at 25° C. and 60% relative humidity and analyzed via the DelsaNano C particle size analyzer using a dynamic light scattering technique at 25° C.

TABLE 8

| Formulation | 1 day | 3 month | 6 month |
| --- | --- | --- | --- |
| Lyophilized powder | | | |
| 0.500 g probucol + 0.150 g sucrose laurate | 173 | 191 | 192 |
| 1.000 g probucol + 0.25 g sucrose laurate | 174 | 203 | 192 |
| 0.500 g danazol + 0.375 g sucrose laurate | 231 | 240 | 221 |
| 1.000 g danazol + 0.500 g sucrose laurate | 265 | 278 | 286 |
| Spray dried powder | | | |
| 0.500 g probucol + 0.125 g sucrose laurate | 183 | 191 | 191 |
| 1.000 g probucol + 0.250 g sucrose laurate | 206 | 206 | 208 |
| 0.500 g danazol + 0.375 g sucrose laurate | 250 | 261 | 253 |
| 1.000 g danazol + 0.500 g sucrose laurate | 265 | 253 | 275 |

As seen in Table 8, there is no significant difference in particle size of the redispersed solids when analyzed after one day's storage, after 3 months' storage, and after 6 months' storage. Although an increase in particle size was observed with the lyophilized powders of probucol and danazol from after 1 day to after 3 months, the change was insignificant. It can be concluded from this stability study that the dried powders with sucrose laurate as stabilizer have stability for at least 6 months in appropriate storage conditions without change in particle size of the redispersed solids.

Figure 12:
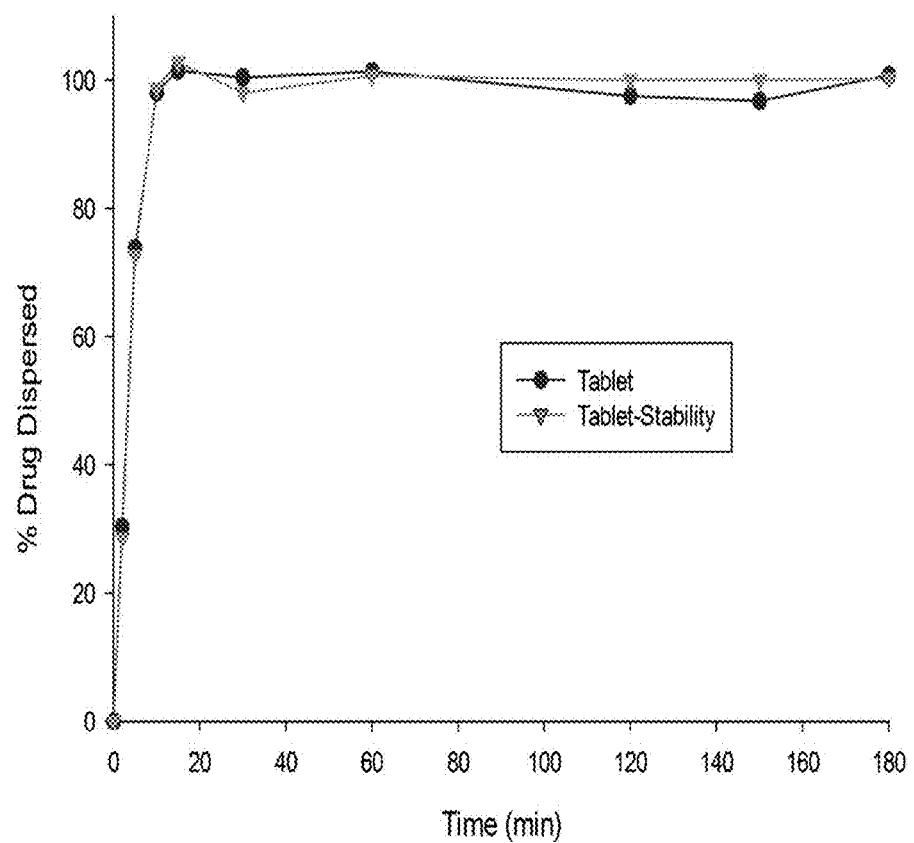
FIG. 12 shows the results of a dispersion test of a tablet containing probucol as a model drug kept on stability study at 25° C./60% relative humidity.

In addition, with reference to FIG. 12, tablets containing lyophilized probucol nanoparticles were prepared. Specifically, lyophilized samples corresponding to 20 mg of drug were weighed and mixed with 2% sodium lauryl sulfate and 5% Kollidon® CL. Lactose was added as a diluent. Subsequently, tablets, with the weight of ca. 150 mg each, were compressed at pressures of 2.1±0.2 MPa using 8 mm flat face punches on a single punch Carver Press assembly. The prepared tablets were subjected to immediate redispersion in aqueous media and redispersion in aqueous media after 3 months' storage at 25° C. and 60% relative humidity. As seen in FIG. 12, was no difference observed in dispersion profile between freshly prepared tablets and tablets stored for 3 months at appropriate conditions.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional, or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A method for preparing a solid dosage form containing nanoparticles, the method comprising the steps of:
    (a) reducing particle size of at least one pharmaceutically active ingredient dispersed in a solution containing a sugar ester nanoparticle stabilizer to form a nanosuspension; and
    (b) drying the nanosuspension of step (a) to form the solid dosage form,
    wherein the sugar ester nanoparticle stabilizer is a sugar fatty acid ester, and
    wherein no excipient other than the sugar ester nanoparticle stabilizer is added for stabilizing the nanoparticles, and wherein the ratio of the total amount of the sugar ester nanoparticle stabilizer to the total amount of the pharmaceutically active ingredient in the solid dosage form is equal to or less than 1:1.

2. The method of claim 1, wherein the sugar fatty acid ester comprises a medium chain fatty acid.

3. The method of claim 2, wherein the medium chain fatty acid is selected from the group consisting of caproic acid, caprylic acid, capric acid, lauric acid, fatty acids with aliphatic tails of 6 to 12 carbons, and combinations thereof.

4. The method of claim 3, wherein the sugar fatty acid ester is sucrose laurate or lactose laurate.

5. The method of claim 1, wherein the sugar ester nanoparticle stabilizer is a combination of more than one sugar ester fatty acid.

6. The method of claim 1, wherein the solid dosage form is prepared without use of sonication.

7. The method of claim 1, wherein particle size of the at least one pharmaceutically active ingredient after step (a) but prior to step (b) is an original nanoparticle size, and wherein particle size of the at least one pharmaceutically active ingredient after redispersion of the solid dosage form in aqueous media is equivalent to the particle size of the at least one pharmaceutically active ingredient after step (a) but prior to step (b).

8. A solid dosage form containing nanoparticles made by a method comprising the steps of:
    (a) reducing particle size of at least one pharmaceutically active ingredient dispersed in a solution containing a sugar ester nanoparticle stabilizer to form a nanosuspension; and
    (b) drying the nanosuspension of step (a) to form the solid dosage form,
    wherein the sugar ester nanoparticle stabilizer is a sugar fatty acid ester, and
    wherein no excipient other than the sugar ester nanoparticle stabilizer is added for stabilizing the nanoparticles, and wherein the ratio of the total amount of the sugar ester nanoparticle stabilizer to the total amount of the pharmaceutically active ingredient in the solid dosage form is equal to or less than 1:1.

9. The solid dosage form of claim 8, wherein the sugar fatty acid ester comprises a medium chain fatty acid.

10. The solid dosage form of claim 9, wherein the medium chain fatty acid is selected from the group consisting of caproic acid, caprylic acid, capric acid, lauric acid, fatty acids with aliphatic tails of 6 to 12 carbons, and combinations thereof.

11. The solid dosage form of claim 10, wherein the sugar fatty acid ester is sucrose laurate or lactose laurate.

12. The solid dosage form of claim 8, wherein the sugar ester nanoparticle stabilizer is a combination of more than one sugar ester fatty acid.

13. The solid dosage form of claim 8, wherein particle size of the at least one pharmaceutically active ingredient after step (a) but prior to step (b) is an original nanoparticle size, and wherein particle size of the at least one pharmaceutically active ingredient after redispersion of the solid dosage form in aqueous media is equivalent to the particle size of the at least one pharmaceutically active ingredient after step (a) but prior to step (b).

14. The solid dosage form of claim 13, wherein the particle size is equivalent after storage at 25° C. and 60% relative humidity for at least six months.

15. A nanosuspension comprising nanoparticles of at least one pharmaceutically active ingredient dispersed in a solution containing a sugar ester nanoparticle stabilizer wherein the sugar ester nanoparticle stabilizer is a sugar fatty acid ester, and wherein no excipient other than the sugar ester nanoparticle stabilizer is added to stabilize the nanosuspension, and wherein the ratio of the total amount of the sugar ester nanoparticle stabilizer to the total amount of the pharmaceutically active ingredient in the solid dosage form is equal to or less than 1:1.

* * * * *